United States Patent [19]

Caspari et al.

[11] Patent Number: 5,336,266
[45] Date of Patent: Aug. 9, 1994

[54] KNEE JOINT PROSTHESIS

[76] Inventors: Richard B. Caspari, 2192 Sheppard Town Rd., Maidens, Va. 23102; Jeffrey G. Roberts, 3688 Montclair Dr., Palm Harbor, Fla. 34684; James T. Treace, 2701 Bluffs Dr., Largo, Fla. 34640

[21] Appl. No.: 773,410

[22] Filed: Oct. 9, 1991

Related U.S. Application Data

[62] Division of Ser. No. 462,528, Jan. 8, 1990, Pat. No. 5,171,276.

[51] Int. Cl.$^5$ .............................................. A61F 2/38
[52] U.S. Cl. .................................................. 623/20
[58] Field of Search .................... 623/16, 18, 19, 20, 623/22, 23

[56] References Cited

U.S. PATENT DOCUMENTS

| | | |
|---|---|---|
| D. 245,259 | 8/1977 | Shen . |
| D. 248,771 | 8/1978 | Groth, Jr. et al. . |
| 3,852,830 | 12/1974 | Marmor . |
| 3,953,899 | 5/1976 | Charnley . |
| 3,958,278 | 5/1976 | Lee et al. . |
| 4,000,525 | 1/1977 | Klawitter et al. . |
| 4,034,418 | 7/1977 | Jackson et al. . |
| 4,055,862 | 11/1977 | Farling . |
| 4,085,466 | 4/1978 | Goodfellow et al. . |
| 4,193,140 | 3/1980 | Treace . |
| 4,207,627 | 6/1980 | Cloutier . |
| 4,211,228 | 7/1980 | Cloutier . |
| 4,219,893 | 7/1980 | Noiles . |
| 4,274,163 | 6/1981 | Malcom et al. . |
| 4,309,778 | 1/1982 | Buechel et al. . |
| 4,340,978 | 7/1982 | Buechel et al. . |
| 4,355,429 | 10/1982 | Mittlemeier et al. . |
| 4,470,158 | 9/1984 | Pappas et al. . |
| 4,531,243 | 7/1985 | Weber et al. . |
| 4,711,639 | 12/1987 | Grundei . |
| 4,714,473 | 12/1987 | Bloebaum ............... 623/20 |
| 4,714,474 | 12/1987 | Brooks, Jr. et al. . |
| 4,728,332 | 3/1988 | Albrektsson . |
| 4,743,261 | 5/1988 | Epinette . |
| 4,769,040 | 9/1988 | Wevers . |
| 4,795,468 | 1/1989 | Hodorek et al. . |
| 4,838,891 | 6/1989 | Branemark et al. . |
| 4,865,607 | 9/1989 | Witzel et al. . |
| 4,888,024 | 12/1989 | Powlan ................. 623/23 |
| 4,892,547 | 1/1990 | Brown .................. 623/20 |
| 4,963,152 | 10/1990 | Hofmann et al. . |
| 4,979,957 | 12/1990 | Hodorek . |

*Primary Examiner*—David Isabella

[57] ABSTRACT

A knee joint prosthesis includes tibial and femoral components and a bearing insert designed for unicompartmental prosthetic total knee replacement and can be implanted using arthroscopic surgical techniques. The tibial and femoral prosthesis components have channels or portals therethrough allowing supply of cement to the prosthesis-bone interface after the prosthesis has been positioned for implant. Recesses communicate with the channels and cooperate with the bone surfaces to form cement receiving chambers, and rims at least partially surround the recesses to penetrate the bone surfaces to stabilize the positions of the prostheses and form seals preventing cement from escaping from the prosthesis-bone interfaces.

10 Claims, 2 Drawing Sheets

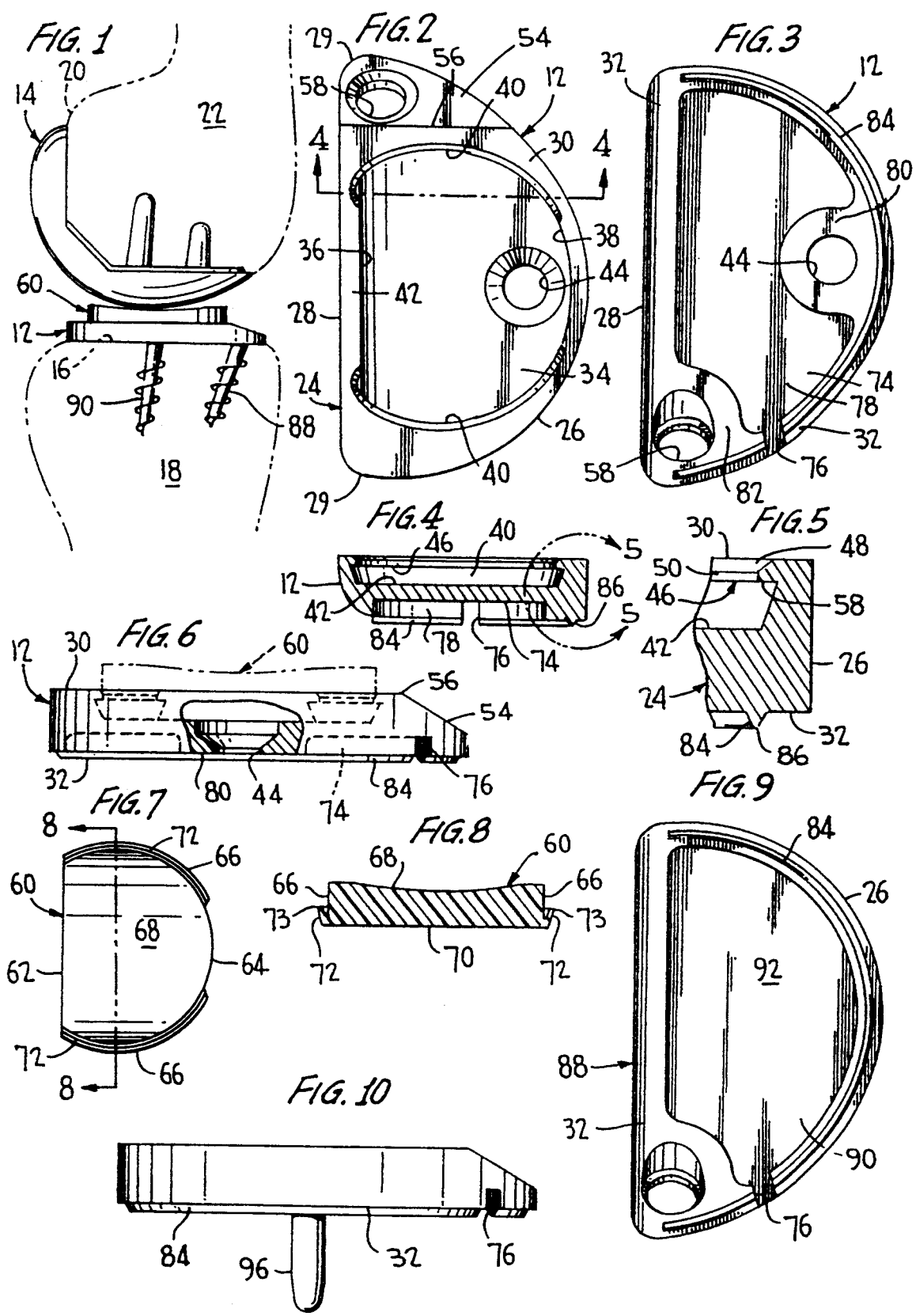

KNEE JOINT PROSTHESIS

This is a divisional application of application Ser. No. 07/462,528 filed Jan. 8, 1990, now U.S. Pat. No. 5,171,276.

FIELD OF THE INVENTION

The present invention relates broadly to prosthetic implants, and more particularly, to prostheses for human joints, such as the knee, implantable by means of arthroscopic as well as open surgical techniques.

DISCUSSION OF THE PRIOR ART

Previous proposals for artificial knee prostheses including components for surgical implantation into a patient's knee are known in the art. The complexity of normal knee movement, however, has rendered the attainment of natural knee action quite difficult. More specifically, the natural knee joint includes the bottom part of the femur, constituted by the two condyles, the lower parts of which bear upon the complementary shaped upper surface plateaus of the tibia through the intermediary of cartilage or meniscus. Connection through the knee is provided by means of ligaments which also provide joint stability and assist in absorbing stresses applied to the knee. The femur, cartilage and tibia are normally subjected to significant compression loading in supporting the weight of the body.

Movement of the normal knee is not a true hinged joint about a single center but, rather, is a complex action including rocking, gliding and axial rotation. During the first part of the knee movement from full extension of the leg towards flexion, there is pivotal rotation of the tibia about the femur, which is then converted to a rocking movement wherein the femoral condyles roll posteriorly on the tibial plateaus. The rocking movement then changes to a combined sliding and pivoting movement wherein successive points on the femoral condyles slide forward on the tibial plateaus until full flexion is obtained. In other words, the flexion movement is polycentric, that is, about different centers which are not fixed in one position but lie in a somewhat spiral or polycentric pathway.

A variety of total knee prostheses have been proposed, essentially being of two broad types, hinged and non-hinged. Knee prostheses of the first category possess significant disadvantages in that they generally involve the removal of natural ligaments and only permit motion about a single axis as opposed to the controlled rotation and translation characteristic of a natural, healthy knee.

Knee prostheses of the second type generally include femoral components secured to the condylar surfaces of the femur, typically having cylindrical bearing surfaces, and tibial components fixed to the tibial plateaus, the femoral components bearing against the upper surfaces of corresponding tibial components. Examples of prostheses of the latter type are shown in U.S. Pat. No. 4,470,158 to Pappas et al; U.S. Pat. No. 4,211,228 to Cloutier; U.S. Pat. No 4,207,627 to Cloutier; and U.S. Pat. No. 3,953,899 to Charnley.

In addition to total knee replacement, unicompartmental knee replacement is known wherein a single compartment of the knee is surgically restored. Typically, the medial or lateral portion of the tibio-femoral joint is replaced without sacrificing normal remaining structure in the knee. For instance, U.S. Pat. No. 4,340,978 to Buechel et al discloses a unicompartmental knee replacement device including a tibial platform secured to the tibia and having a track for receiving a bearing insert. A femoral component is attached to one of the condylar surfaces of the femur and is provided with a generally convex spherical inferior surface for engaging the superior surface of the bearing insert. Similar unicompartmental knee implants are shown in U.S. Pat. No. 4,743,261 to Epinette; U.S. Pat. No. 4,309,778 to Buechel et al; U.S. Pat. No. 4,193,140 to Treace; U.S. Pat. No. 4,034,418 to Jackson et al; and U.S. Pat. No. 3,852,830 to Marmot.

The non-hinged knee implants previously discussed, while possessing advantages over the hinged devices, nonetheless are characterized by numerous drawbacks. Many of the prior art prostheses require the removal of a great deal of bone from the femur and tibia in order to accommodate the implant, thus complicating and prolonging the surgical procedure and reducing the amount of bone available in reserve should subsequent restorative measures be required. Additionally, alignment of the prosthesis components is extremely difficult, and even small misalignments lead to an imbalance of the forces transmitted from the femoral component to the tibial component. The asymmetric distribution of load on the plateaus of the tibial component can result in tibial loosening and failure of the prosthesis. Moreover, inadequate fixation of the prosthesis can occur, possibly resulting in the prosthesis twisting loose from the implanted position.

The misalignment and anchoring problems associated with conventional prostheses are due in part to the fact that the prosthesis is secured in place by means of cement applied to the prothesis after a trial fit and prior to actual fixation. Although the joint may have been precisely prepared to accept the prosthesis, and although the femoral and tibial components may have been accurately aligned during trial fitting, deviation from the desired location is apt to occur when the prosthesis is removed to place cement on the prepared bone surface and then replaced on the bone surface.

The prior art prosthetic devices have another disadvantage in that excess cement tends to escape from between the bone and the implant around the edges of the implant. The excess cement, if not removed, may deteriorate and crumble, thereby becoming a source of possible irritation. Additionally, cracking and breakage of the cement may lead to loosening of the cement bond, thus jeopardizing the integrity of the cemented parts. Therefore, additional steps are typically undertaken to remove the excess cement squeezed out during the surgical procedure.

Several of the prior art prosthetic devices previously referred to are illustrative of the foregoing deficiency. For example, Buechel et al ('978) is directed to a unicompartmental knee prosthesis wherein the prosthesis components must be removed after a satisfactory trial fit to allow cement to be placed on the bone surfaces. The components are then reintroduced into the surgical site, located in the pre-established position and firmly held in compression with the bone until complete polymerization has been obtained. Excess cement is removed from the edges of the prosthetic component by a scalpel and curette. Similarly, Charnley teaches inserting cement through a hole cut into the head of the tibia. The anterior end of the tibial component is then elevated to cause the posterior end to press into the tibia bone so as to close the posterior route of escape for the cement. Treace discloses a knee prosthesis for fixation to the femur including a curved body provided with a plurality of cement holding rings fixedly attached to and extending upwardly from the upper surface of the body. The femur must be prepared by drilling slots therein for receiving the cement holding rings subsequent to cement being injected into the slots.

SUMMARY OF THE INVENTION

Accordingly, it is a primary object of the present invention to overcome the above mentioned disadvantages of the prior art.

Another object of the present invention is to provide a prosthesis permitting cement to be supplied between the prosthesis and the prepared tissue surface after the prosthesis has been positioned on the tissue surface.

A further object of the present invention is to provide a prosthesis which can be implanted utilizing arthroscopic surgical techniques.

An additional object of the invention is to utilize a rim to control rotation of a femoral prosthesis during fixation by cement.

The present invention has another object in that unicompartmental prosthetic total knee replacement can be performed with the use of modular tibia components, bearing inserts and femoral components.

Another object of the invention is to provide a tibial prosthesis receiving bearing inserts of varying thicknesses to provide accurate alignment.

According to the present invention, therefore, a prosthesis includes a body having a fixation surface for placement adjacent the surface of the tissue, such as bone, to which the prosthesis is to be affixed. A recess is formed in the fixation surface of the body such that, when the fixation surface is positioned adjacent the bone surface, the recess is substantially closed off by the bone surface to define a cement receiving chamber. Securing means such as a screw or post member secures the body member in position on the bone surface. A channel formed in the prosthetic body establishes communication between the cement receiving chamber and the exterior of the body member, and cement is introduced into the cement receiving chamber via the channel. Thus, the prosthesis may be cemented in place while in the desired position and secured against movement. The invention further contemplates a wall or rim extending from the fixation surface for penetrating the bone surface when the prosthesis is in position thereon so as to provide additional stability. The rim extends along and at least partially surrounds the recess to serve as a seal or trap for preventing release of cement from the cement receiving chamber thereby augmenting cement pressurization.

Some of the advantages of the present invention over the prior art are that the prostheses can be placed using arthroscopic surgical techniques, textured surfaces enhance the prosthesis-cement interface, the asymmetrical shade of the tibial prosthesis component provides optimal coverage of the tibial plateau, the modular design allows variation of final tibial thickness, the femoral prosthesis component does not interfere with the patella, two spaced tapered posts on the femoral prosthesis component provide rotational stability, a rim extending along a recess in the fixation surface of the femoral prosthesis component resists rotation of the implant and augments cement pressurization, a rim extending along a recess in the fixation surface of the tibial prosthesis component holds the implant in place and augments cement pressurization, and a portal or channel through the tibial and femoral prosthesis components allows placement of bone cement between the implant and the prepared bone surface after the implant has been accurately positioned on the bone surface without moving the implant.

Other objects and advantages of the present invention will become apparent from the following description of the preferred embodiments taken in conjunction with the accompanying drawings.

BRIEF DESCRIPTION OF THE DRAWINGS

FIG. 1 is a side view of the knee joint prosthesis of the present invention with the femur and tibia shown in phantom.

FIG. 2 is a top plan view of the tibial prosthesis component of the present invention.

FIG. 3 is a bottom plan view of the tibial prosthesis component of FIG. 2.

FIG. 4 is a cross-section of the tibial prosthesis component taken along line 4—4 of FIG. 2.

FIG. 5 is an enlarged fragmentary view taken along line 5—5 of FIG. 4.

FIG. 6 is a broken side view of the tibial prosthesis component with a bearing insert shown in phantom.

FIG. 7 is a top view of a bearing insert of the present invention.

FIG. 8 is a section of the bearing insert taken along line 8—8 of FIG. 7.

FIG. 9 is a bottom plan view of another embodiment of the tibial prosthesis component of the present invention.

FIG. 10 is a side view of a further embodiment of the tibial prosthesis component of the present invention.

DESCRIPTION OF THE PREFERRED EMBODIMENT

Figure 11:
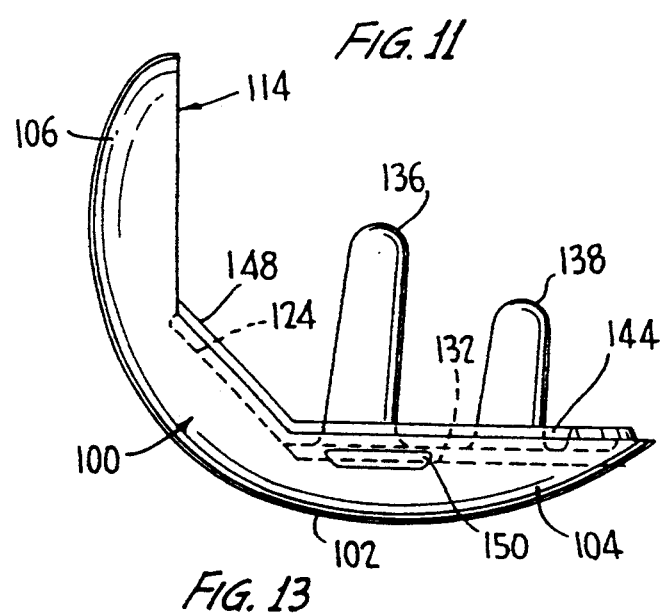
FIG. 11 is a side view of the femoral prosthesis component of the present invention.

The present invention relates to prostheses for implant in the body and is particularly described in connection with a prosthesis or implant for the knee joint. A preferred embodiment for a knee joint prostheses implant according to the present invention is shown in FIG. 1 and includes a tibial prosthesis component 12, a femoral prosthesis component 14 and a bearing insert 60. The tibial component 12 is affixed to a suitably prepared site on the upper plateau 16 of the tibia 18, shown in phantom. The femoral component 14 is affixed to a suitably prepared site on a condyle 20 of a femur 22, shown in phantom.

FIGS. 2–6 show a preferred embodiment of the tibial component 12 including a body 24 which, viewed from the top, has a generally asymmetrical, D-shaped configuration with an arcuate side wall 26 joined to a generally planar side wall 28 via curved side wall sections 29. The body 24 has a top or upper surface 30 connecting the upper edges of the planar side wall 28, the arcuate side wall 26 and the curved side wall sections 29. As best shown in FIG. 3, the body has a bottom or fixation surface 32 connecting the lower edges of the planar side wall 28, the arcuate side wall 26 and the curved side wall sections 29.

A cavity 34 is formed in the top surface 30 of the body 24 defined by a planar cavity side wall 36 joined to an arcuate cavity side wall 38 by curved cavity wall end sections 40 and a cavity bottom wall 42 joining the lower edges of cavity side walls 36, 38 and 40. An inwardly tapered through hole 44 is formed in the cavity bottom wall 42 and extends substantially perpendicularly through the body 24.

With particular reference to FIGS. 2 and 4, each curved cavity wall end section 40 has a lip 46 projecting from the curved cavity wall section into the interior of the cavity 34. As shown in detail in FIG. 5, the lip 46 has a chamfered surface 48 extending downwardly from the top surface 30 of the body at an angle of approximately 45°. The surface 48 terminates in a vertical cavity facing surface 50 which joins curved cavity wall section 40 via a horizontal surface 52. Curved cavity wall sections 40 extend downwardly from horizontal surface 52 to cavity bottom wall 42 at an angle of approximately 20° toward the interior of the cavity 34 such that lips 46 form grooves in the side wall curved end sections 40.

With reference to FIG. 6, it can be seen that the top surface 30 of the body 24 is generally flat except for a sloping surface 54 at an anterior portion extending from a straight edge 56 located on the top surface downwardly at an angle of approximately 30° with respect to the parallel top and bottom surfaces to meet the side walls of the body. A through hole 58 is formed in the anterior portion to extend through the body from sloping surface 54 to bottom surface 32 at an angle of approximately 60° with respect to the bottom surface 32 and perpendicular to surface 54.

A bearing insert 60 closely configured to the peripheral dimensions of the cavity 34, as defined by cavity side wall sections 36, 38 and 40, includes a body defined by a planar insert side wall 62 joined to an arcuate insert side wall 64 by curved insert wall end sections 66. The body has an upper surface 68 joining the upper ends of the insert side walls 62, 64 and 66, while the lower ends of the side walls are joined by a lower surface 70.

Upper surface 68 is slightly concave when viewed from the side, as shown in FIGS. 6 and 8. Each curved end section 66 is provided with a flexible protruding lip 72 extending upwardly and outwardly from the lower surface 70 toward the upper surface 68 at an angle of approximately 20° with respect to the end section 66, as best illustrated in FIG. 8, to terminate in an upper edge 73 spaced from the side wall curved end section 66. The insert 60 has a configuration mating with the configuration of cavity 34 and is received in the cavity 34, as shown in phantom in FIG. 6, with the insert bottom surface 70 resting on the cavity bottom wall 42, insert side walls 62, 64 and 66 in close abutment with the respective cavity side walls 36, 38 and 40 and the lips 72 engaged in the grooves beneath lips 46 to securely retain the insert in position within the cavity. A range of inserts ranging in thickness, for example, from approximately 8mm to 15mm as measured from the insert upper surface 68 to the insert lower surface 70, is provided so that the proper fit can be attained. The upper surface 68 of the insert will be elevated with respect to the top surface 30 of the tibial component body by varying amounts depending upon the thickness of the particular insert. Preferably, the bearing insert is integrally fabricated in a unitary manner of ultra-high molecular weight polyethylene.

As particularly shown in FIG. 3, the fixation surface 32 of the body 24 has a recess 74 therein defined within the confines of the side walls 26, 28 and 29 of the body. A channel or portal 76 connects the recess 74 to the exterior of the body and extends from the recess 74 through the arcuate side wall 26 at the anterior portion of the body. The recess 74 and the channel 76 share a common end wall 78 which defines the depth to which the recess and channel extend above the bottom surface 32 into the interior of the body. A land 80 along the fixation surface 32 isolates the through hole 44 from the recess 74, while a land 82 along the fixation surface 32 isolates the through hole 58 from the recess 74. A rim 84 projects from the bottom surface 32 spaced from but following the curve of arcuate side wall 26 with an interruption at the location of channel 76. As is most clearly depicted in FIGS. 4 and 5, the rim 84 is triangular in cross-sectional configuration, with the apex of the triangle forming a sharp bottom/host edge 86 for the body. The rim 84 defines a wall extending along the recess 74 and at least partially surrounding the recess.

The tibial component 12 is provided in a range of sizes, for example, with the dimension A of the body ranging from approximately 37.5mm to approximately 54mm and the dimension B ranging from approximately 21mm to approximately 33mm, as shown in FIG. 2, to accommodate a range of sizes for optimal coverage of the tibial plateau. The asymmetrical "D" configuration of the body further contributes to optimal tibial plateau coverage in order to present a contact area for the femoral component coinciding with that of a normal knee.

The tibial component 12 is particularly designed to be affixed to a suitably prepared tibial plateau through arthroscopic surgical techniques; however, the tibial component can be used in normal open surgery procedures for prosthetic knee replacement. In use, the body can be grasped by an appropriate surgical instrument and placed in position on the tibial plateau with the bottommost edge 86 resting upon the tibial plateau. Once the desired position for the body on the tibial plateau has been established, the body is affixed by a cancellous bone screw 88 inserted at an angle through hole 58 and into the anterior portion of the tibia as illustrated in FIG. 1. A second cancellous bone screw 90 can be inserted through the body into the tibia via through hole 44 if desired. The recess 74 formed in the bottom surface 32 of the body define, together with the tibial plateau, an enclosed cement receiving chamber which communicates with the exterior of the body through channel 76. A bone cement, preferably low viscosity methyl-methacrylate, is injected into the chamber through channel 76 to form a physical bond between the body and the tibial plateau. It can be seen, therefore, that the tibial component can properly be positioned prior to the application of cement and need not be moved or disturbed in any manner thereby assuring precise and accurate positioning. The cement can be inserted in the cement receiving chamber by means of a needle or syringe to be compatible with arthroscopic techniques. The rim 84 forms a seal around the cement receiving chamber with respect to the tibial plateau to augment filling of the cement receiving chamber, and the rim 84 penetrates the tibial surface to establish a seal preventing escape of cement from the chamber while the bottom surface 32 engages the tibial plateau. Additionally, the rim 84 stabilizes the position of the tibial component on the tibial plateau. The lands 80 and 82 along the bottom surface 32 isolate the respective fixation screws from the cement so that the screws can be removed, if necessary. The bottom surface 32 and the wall 78 of recess 74 are textured to enhance the interface between the body and the cement. The invention contemplates a right medial/left lateral orientation for the tibial component in addition to the left medial/right lateral illustrated herein. A suitable bearing insert 60 can be inserted after the body has been implanted, or the insert 60 can be mounted in the body prior to implanting the body.

Another embodiment of a tibial component according to the present invention is shown in FIG. 9 wherein a body 88 is essentially the same as body 24 except that through hole 44 has been eliminated and the recess 90 follows the arcuate wall 26, as does end wall 92. The body 88 thus accommodates only a single screw which, due to its position at the anterior portion of the implant, provides sufficient fixation.

A further embodiment of the present invention is shown in FIG. 10 and is essentially the same as the tibial component of FIG. 9 except that a post 96 depends from the end wall 92 of the recess 90 at substantially the same position as through hole 44 shown in FIG. 3. The post 96 is intended to be inserted into a corresponding drilled hole in the tibial plateau. Preferably, the post 96 is tapered to allow a press fit into the corresponding hole.

The femoral component 14 of the prosthesis of the present invention is illustrated in FIG. 11–15 and includes a body 100 having a curved configuration defining an arcuate outer bearing surface 102 with an anterior or distal end 104 and a posterior end 106. The bearing surface 102 is generally polycentric, that is, the surface lies on arcs of circles having more than one center and more than one radius to approximate the natural articulating surface of a femoral condyle. The posterior end 106 curves somewhat sharply while the anterior end 104 curves somewhat gradually. In other words, the radius of an imaginary circle in which the anterior end 104 lies is greater than the radius of an imaginary circle in which the posterior end 106 lies. Body 100 further includes an inner fixation surface which joins the bearing surface 102 at side and end edges. The fixation surface includes a planar posterior section 118, a planar chamfer section 120 and a planar distal section 122. The posterior and distal sections 118 and 122 are oriented substantially perpendicular with respect to each other, while chamfer section 120 is oriented at an angle of substantially 45° with respect to the posterior and distal sections.

Figure 12:
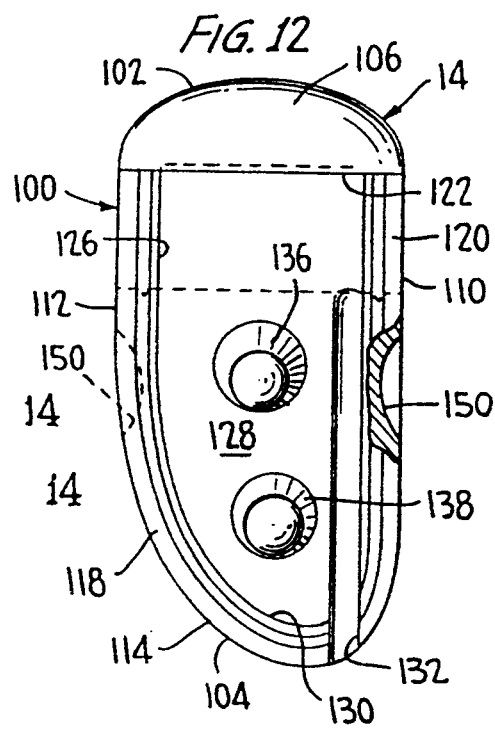
FIG. 12 is a top view of the femoral prosthesis component of FIG. 11.

As shown in the top view of the femoral component 14 in FIG. 12, the body 100 has a generally straight medial side edge 110 and a generally straight lateral side edge 112 parallel to edge 110 but about one half the length of the edge 110. The side edge 112 is joined to side edge 110 via a generally polycentric curved edge 114. An arcuate posterior edge 116 joins the opposite ends of the side edges 110 and 112. Side edge 110 extends along the sides of the posterior, chamfer and distal sections of the fixation surface. Side edge 112 extends along the sides of the posterior and chamfer sections and along a portion of the side of the distal section, the curved edge 114 extending along the remaining portion of the side of the distal section.

As shown in FIGS. 11 and 12, a recess 124 is formed in the chamfer section 120 and the distal section 122 of the fixation surface. A side wall 126 of the recess 124 generally follows the side edges 110, 112 and 114 of the body 100, running generally parallel thereto but separated therefrom by a portion of the fixation surface. The recess is provided with a bottom surface 128 and terminates along a bottom edge 130 of the posterior section 118. A channel 132 is formed in the bottom surface 128 of the recess 124 extending generally parallel to the side edge 110 of the body 100 in the distal section 122 and through the curved side edge 114 of the body to establish communication with the exterior.

Figure 13:
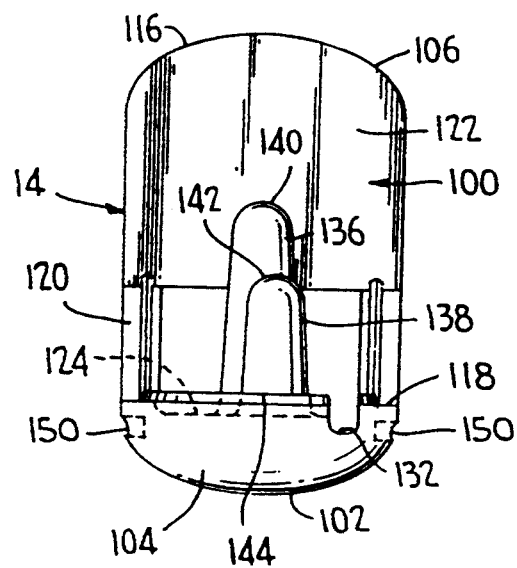
FIG. 13 is an anterior view of the femoral prosthesis component of FIG. 11.
Figure 14:
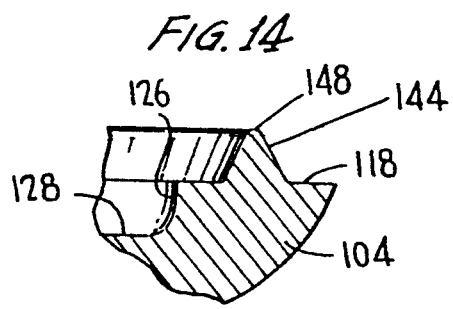
FIG. 14 is an enlarged fragmentary view in section taken along line 14—14 of FIG. 11.

Posts 136 and 138 project upwardly substantially perpendicular to bottom surface 128, preferably at an inclination of 5° from the plane of the posterior section 118. The posts 136 and 138 are generally cone-shaped and have respective tapered top ends 140 and 142. As depicted in FIG. 11, the post 136 is longer than the post 138, the post 138 being around two-thirds the length of post 136. A rim 144 projects from the fixation surface, spaced from but lying generally parallel to side edges 110, 112 and 114 of the body 100. As can be seen in FIG. 12, the rim 144 also lies generally parallel to the side wall 126 of the recess 124 so as to at least partially surround the recess 124 along the chamfer section 120 and the distal section 122. The rim 144 is preferably triangular in cross-sectional configuration to provide a relatively sharp edge 148 as was discussed in connection with rim 84 for the tibial component 12 and as shown in FIG. 14. A semi-circular indentation 150 is provided on each side of the body 100 in distal section 122 proximate side edges 110 and 112 as shown in FIGS. 11, 12 and 13.

The femoral component 14 is adapted to be positioned on a condylar surface of the femur after the surface has been suitably cut and shaped to conform to the fixation surface of the body 100. The femoral component may be positioned by means of open or arthroscopic surgical techniques with the indentations 150 engaged by a surgical tool for placement of the femoral component on the prepared femoral condyle. The posts 136 and 138 are fitted into drilled holes in the cut distal end of the femoral condyle, the tapered upper ends 140 and 142 of the posts allowing for a press fit. With the femoral component in the proper position on the femoral condyle, the rim 144 penetrates the bone to enhance securement and forms a seal with respect to the bone around the cement receiving chamber formed by the recess 124 and the surface of the bone. Cement is introduced into the chamber through the channel 132 by means of a syringe, a needle or the like as discussed in connection with the tibial component. The rim 144 inhibits rotation of the femoral component as do the posts 136 and 138. Preferably, the fixation surface and the recess bottom surface 128 are textured to enhance the interface between the femoral component and the cement. The tibial and femoral components are preferably fabricated of metal, the preferred material for the tibial component being implant grade titanium, and for the femoral component cobalt-chromium.

The surface 102 of the femoral component cooperates with the concave surface 68 of bearing insert 60 to allow the same freedom of movement afforded by a healthy knee. The non-metallic insert 60 provides a bearing surface for the metallic femoral component similar to the cartilage in a natural knee joint. The plastic material from which the insert is fabricated provides a low coefficient of friction between the contacting surfaces and minimizes the rate of wear of the contacting surfaces of the components. As discussed in connection with the tibial component, it is contemplated that the femoral component be available in a number of sizes, and in right medial/left lateral and left medial/right lateral versions to prevent interference with the patella.

The knee joint prosthesis of the present invention can be used in conventional open, total knee replacement surgical procedures but is particularly useful for implant using arthroscopic surgical techniques due to the simplified cementing procedures and the stability permitted by the tibial and femoral prosthesis components coupled with the modular nature thereof and the use of bearing inserts of varying sizes to produce desired tibial thicknesses or heights. Method and apparatus for implant of the knee joint prosthesis of the present invention are disclosed in an application filed concurrently herewith by the same inventors, entitled "Methods and Apparatus for Arthroscopic Prosthetic Knee Replacement", the disclosure of which is incorporated herein by reference.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A prosthesis for implant on the femoral condyle of the knee comprising
    a body having an outer curved bearing surface and an inner surface for engaging the femoral condyle including a planar distal portion and a planar posterior portion disposed at an angle relative to said planar distal portion;
    recess means in said inner surface for forming a space between said body and the femoral condyle; and
    means in said body communicating with said recess means for supplying cement to fill said space with said inner surface engaging the femoral condyle.

2. A prosthesis as recited in claim 1 wherein said distal portion of said inner surface is disposed substantially transverse to said posterior portion of said inner surface.

3. A prosthesis as recited in claim 2 wherein said inner surface includes a planar chamfer portion disposed between said distal and posterior portions.

4. A prosthesis as recited in claim 3 wherein said chamfer portion is disposed at angles of substantially 45° to said distal and posterior portions.

5. A prosthesis as recited in claim 4 further comprising spaced tapered posts extending from said distal portion of said inner surface.

6. A prosthesis as recited in claim 5 wherein said recess means is disposed in said distal and chamfer portions of said inner surface.

7. A prosthesis as recited in claim 6 wherein said body includes rim means extending from said inner surface along said recess means for penetrating the femoral condyle.

8. A prosthesis as recited in claim 7 wherein said cement supplying means includes a channel extending from said outer surface to said recess means.

9. A prosthesis as recited in claim 8 wherein said channel extends along said recess means in said distal portion of said inner surface to said recess means in said chamfer portion of said inner surface.

10. A prosthesis as recited in claim 1 wherein said body includes rim means extending from said inner surface for penetrating the femoral condyle.

* * * * *